US006613352B2

(12) United States Patent
Lagace et al.

(10) Patent No.: US 6,613,352 B2
(45) Date of Patent: *Sep. 2, 2003

(54) LOW-RIGIDITY LIPOSOMAL FORMULATION

(75) Inventors: Jacqueline Lagace, St-Laurent (CA); Christian Beaulac, Yamachiche (CA); Sebastien Clement-Major, St.-Lambert (CA)

(73) Assignee: Universite de Montreal, Montreal (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1 day.

This patent is subject to a terminal disclaimer.

(21) Appl. No.: 09/291,681

(22) Filed: Apr. 13, 1999

(65) Prior Publication Data

US 2001/0006660 A1 Jul. 5, 2001

(51) Int. Cl.[7] .............................................. A61K 9/127
(52) U.S. Cl. ......................... 424/450; 264/4.1; 264/4.3
(58) Field of Search ........................... 424/450; 935/54; 264/4.1, 4.3, 4.6

(56) References Cited

U.S. PATENT DOCUMENTS

| 4,235,871 A | 11/1980 | Papahadjopoulos et al. |
| 4,588,578 A | 5/1986 | Fountain et al. |
| 4,610,868 A | 9/1986 | Fountain et al. |
| 4,708,861 A | 11/1987 | Popescu et al. |
| 4,737,323 A | 4/1988 | Martin et al. |
| 4,752,425 A | 6/1988 | Martin et al. |
| 4,753,788 A | 6/1988 | Gamble |
| 4,812,312 A | * 3/1989 | Lopez-Berestein et al. .. 424/450 |
| 4,822,777 A | 4/1989 | Abra |
| 4,880,635 A | 11/1989 | Janoff et al. |
| 4,895,719 A | 1/1990 | Radhakrishnan et al. |

(List continued on next page.)

FOREIGN PATENT DOCUMENTS

| WO | WO 85/00515 | 2/1985 |
| WO | WO 85/00751 | 2/1985 |
| WO | WO 86/01103 | 2/1986 |

(List continued on next page.)

OTHER PUBLICATIONS

American Society for Microbiology, Manual Of Methods For General Bacteriology, Washington, D.C. p. 185, 1981.

Angus et al., "Outer Membrane Permeability in *Pseudomonas aeruginosa*: Comparison of a Wild–type with an Antibiotic–Supersusceptible Mutant," Antimicrob. Agents Chemother. 21:299–309, 1982.

Bakker–Woudenberg et al., "Efficacy of gentamicin or ceftazidime entrapped in liposomes with prolonged blood circulation and enhanced localization in *Klebsiella pneumoniae*–infected lung tissue" Journal of Infectious Diseased 171:938–947, 1995.

(List continued on next page.)

*Primary Examiner*—Gollamudi S. Kishore
(74) *Attorney, Agent, or Firm*—Clark & Elbing LLP; Kristina Bieker-Brady (57) ABSTRACT

The invention relates to a liposomal formulation that is capable of fusing with cells. The liposomal formulation may contain an agent for delivery to cells. The invention also provides compositions and methods for making the liposomal formulation and for liposomal drug delivery. These include methods of killing microbes and of treatment and prevention of microbial infections through the administration of such a formulation.

20 Claims, 5 Drawing Sheets

U.S. PATENT DOCUMENTS

| | | |
|---|---|---|
| 4,897,384 A | 1/1990 | Janoff et al. |
| 4,927,637 A | 5/1990 | Morano et al. |
| 4,952,405 A | 8/1990 | Yau-Young |
| 4,963,297 A | 10/1990 | Madden |
| 4,973,465 A | 11/1990 | Baurain et al. |
| 4,975,282 A | 12/1990 | Cullis et al. |
| 4,978,654 A * | 12/1990 | Lopez-Berestein et al. ... 514/31 |
| 4,981,692 A | 1/1991 | Popescu et al. |
| 4,994,213 A | 2/1991 | Aitcheson et al. |
| 5,000,887 A | 3/1991 | Tenzel et al. |
| 5,000,958 A | 3/1991 | Fountain et al. |
| 5,006,343 A | 4/1991 | Benson et al. |
| 5,008,050 A | 4/1991 | Cullis et al. |
| 5,023,087 A | 6/1991 | Yau-Young |
| 5,032,582 A | 7/1991 | Abra |
| 5,049,388 A | 9/1991 | Knight et al. |
| 5,049,392 A | 9/1991 | Weiner et al. |
| 5,059,421 A | 10/1991 | Loughrey et al. |
| 5,059,591 A | 10/1991 | Janoff et al. |
| 5,064,655 A | 11/1991 | Uster et al. |
| 5,154,930 A | 10/1992 | Popescu et al. |
| 5,169,637 A | 12/1992 | Lenk et al. |
| 5,180,713 A | 1/1993 | Abra et al. |
| 5,185,154 A | 2/1993 | Lasic et al. |
| 5,194,266 A | 3/1993 | Abra et al. |
| 5,225,212 A | 7/1993 | Martin et al. |
| 5,231,112 A | 7/1993 | Janoff et al. |
| 5,356,633 A | 10/1994 | Woodle et al. |
| 5,399,331 A | 3/1995 | Loughrey et al. |
| 5,409,704 A | 4/1995 | Bally et al. |
| 5,415,867 A | 5/1995 | Minchey et al. |
| 5,429,823 A | 7/1995 | Tremblay et al. |
| 5,508,269 A | 4/1996 | Smith et al. |
| 5,540,936 A | 7/1996 | Coe et al. |
| 5,552,155 A | 9/1996 | Bally et al. |
| 5,578,320 A | 11/1996 | Janoff et al. |
| 5,589,189 A | 12/1996 | Moyihan |
| 5,616,334 A | 4/1997 | Janoff et al. |
| 5,656,287 A | 8/1997 | Adler-Moore et al. |
| 5,660,856 A | 8/1997 | Adler-Moore et al. |
| 5,662,929 A * | 9/1997 | Lagace et al. ... 424/450 |
| 5,670,166 A | 9/1997 | Adler-Moore et al. |
| 5,683,714 A | 11/1997 | Adler-Moore et al. |
| 5,688,525 A | 11/1997 | Adler-Moore et al. |
| 5,693,336 A | 12/1997 | Moynihan |
| 5,756,120 A | 5/1998 | Hersch et al. |
| 5,756,121 A | 5/1998 | Bracken |
| 5,759,571 A | 6/1998 | Hersch et al. |
| 5,766,624 A | 6/1998 | Janoff et al. |
| 5,820,848 A | 10/1998 | Boni et al. |
| 5,830,498 A | 11/1998 | Lenk et al. |
| 5,843,473 A | 12/1998 | Woodle et al. |
| 5,874,104 A | 2/1999 | Adler-Moore et al. |
| 5,891,468 A | 4/1999 | Martin et al. |

FOREIGN PATENT DOCUMENTS

| | | |
|---|---|---|
| WO | WO 86/06959 | 12/1986 |
| WO | WO 87/00043 | 1/1987 |
| WO | WO 87/01933 | 4/1987 |
| WO | WO 87/07530 | 12/1987 |
| WO | WO 88/04573 | 6/1988 |
| WO | WO 91/10422 | 7/1991 |
| WO | WO 91/16882 | 11/1991 |
| WO | WO 92/11842 | 7/1992 |
| WO | WO 93/23015 | 11/1993 |
| WO | WO 94/08565 | 4/1994 |
| WO | WO 94/12155 | 6/1994 |
| WO | WO 94/12156 | 6/1994 |
| WO | WO 94/22430 | 10/1994 |
| WO | WO 94/26253 | 11/1994 |
| WO | WO 95/01777 | 1/1995 |
| WO | WO 95/27478 | 10/1995 |
| WO | WO 96/40061 | 12/1996 |
| WO | WO 99/13816 | 3/1999 |

OTHER PUBLICATIONS

Beaulac et al., "In–vitro bactericidal efficacy of sub–MIC concentrations of liposome–encapsulated antibiotic against Gram–negative and Gram–positive bacteria" Journal of Antimicrobial Chemotherapy 41:35–41, 1998.

Boswell et al., "AmBisome (liposomal amphotericin B): a comparative review" J. Clin. Pharmacol. 38:583–592, 1998.

Grant et al., "Physical biochemistry of a liposomal amphotericin B mixtures used for patient treatment" Biochim. Biophys. Acta 984: 11–20, 1989.

Lagacé et al., "Liposome–encapsulated antibiotics: preparation, drug release and antimicrobial activity against *Pseudomonas aeruginosa*," J. Microencapsulation 8:53–61, 1991.

Lopez–Berestein et al., "Treatment of Hepatosplenic Candidiasis With Liposomal–Amphotericin B," J. Clin. Oncology, 5:310–317, 1987.

Nacucchio et al., "Enhanced liposome–mediated antibacterial activity of piperacillin and gentamicin against gram negative bacilli in vitro," J. Microencapsulation 5:303–309, 1988.

Nicas et al., "*Pseudomonas aeruginosa* Outer Membrane Permeability: Isolation of a Porin Protein F–Deficient Mutant," Bacteriol. 153:281–285, 1983.

Omri et al., "Pulmonary retention of free and liposome–encapsulated tobramycin after intratracheal administration in uninfected rats and rats infected with *pseudomonas aeruginosa*" Antimicrob. Agents Chemother. 38:1090–1095, 1994.

Yoshimura et al., "Permeability of *Pseudomonas aeruginosa* Outer Membrane to Hydrophilic Solutes." J. Bacteriol. 152:636–642, 1982.

* cited by examiner

LOW-RIGIDITY LIPOSOMAL FORMULATION

FIELD OF THE INVENTION

The invention relates to a liposomal formulation that is capable of fusing with cells.

BACKGROUND OF THE INVENTION

Encapsulation of bioactive compounds in natural or synthetic matrixes has been extensively studied over the past decades. Advantages of encapsulation are numerous. First, it provides protection from the inactivation or degradation of the bioactive compound. Secondly, it controls the kinetics of compound release, allowing the optimization of the blood concentration profile. This optimization diminishes the deleterious effects of bioactive compounds with short half lives. In addition, it permits a reduction in toxicity, where relevant.

Liposomes are closed microscopic vesicles that form spontaneously from phospholipids above their transition temperature, in the presence of excess water. Vesicles with diameters ranging from 20 nanometers to several micrometers can be prepared. Multilamellar liposomes are made of concentric phospholipid bilayers separated by aqueous layers. Unilamellar liposomes consist of a single phospholipid bilayer surrounding an aqueous core. Liposomes can accommodate hydrophilic molecules in the aqueous spaces and lipophilic molecules in the lipid bilayers.

The potential of liposomes as vehicles for antimicrobial agents, or therapeutic liposomal formulations, has been studied by several investigators. Successful treatments with liposomes against intracellular bacteria have been demonstrated (Lopez-Berestein et al., 1987, U.S. Pat. No. 4,981, 692). A number of studies have also shown that liposome-entrapped antibacterial agents increase the therapeutic indices of these agents as a result of decreased toxicity, modification of pharmacokinetics and tissue distribution parameters (Lagacé et al., 1991, J. Microencapsulation 8:53–61 and references therein; Omri et al., 1994, Antimicrob. Agents Chemother. 38:1090–1095)

Microorganism resistance to antibiotics is an important health problem world-wide. According to estimates from the United States Center for Disease Control and Prevention, for the period 1980 to 1992, approximately two million hospital-acquired infections occurred annually in the United States, accounting for more than eight million days extended hospital stay and generating more that $4 billion in additional health care costs each year. While overall per capita mortality rates for all diseases declined in the United States from 1980 to 1992, the per capita mortality rate due to infectious disease increased 58% over this period, making infectious diseases the third leading cause of death in the United States. Microbial infections, especially infections caused by difficult-to-treat, antibiotic-resistant microbes, such as bacteria and fungi, cause or contribute to a substantial majority of these deaths.

Microbes use different mechanisms to resist antibiotics. These mechanisms include prevention of the penetration, and/or extrusion, of the drugs from the microbial cells, enzymatic inactivation of the drugs, or alteration of the molecular target. Frequently, multiple mechanisms are present in a synergistic way, thus increasing the degree of resistance. Increasing evidence suggests that acquired antibiotic resistance is often due to a balance between outer membrane penetration rate and the subsequent enzyme inactivation rate. Thus, the outer membrane barrier and the antibiotic-degrading enzymes are strongly synergistic. New generation antibiotics, which can overcome strain-based enzymatic degradation, still do not solve the significant hurdle of penetration through the impermeable microbial membrane or through an exopolysaccharide layer of the microorganism and to its site of action. Recent research reports have also indicated that membranes with a low level of permeability, combined with a multiple drug efflux, play a dominant role in many antibiotic-resistant microorganisms, including *Pseudomonas aeruginosa* (Poole, K. et al., 1996, Antimicrob. Agents Chemother. 40:2021–2028).

The problem of increased resistance to antibiotics is compounded by the misuse of these agents (Merck manual, 1992, 16th Edition, Merck Res. Lab.). For example, because of the antibiotic resistance of microorganisms, which is more acute with older types of antibiotics, practitioners are often prompted to use a newer generation antibiotic, contributing to the increased resistance of microorganisms to these antibiotics. The large scale use of antibiotics in animals, including but not limited to dairy cows, and the presence of these antibiotics in milk, or in the environment, is yet another contributor to increases in microbial resistance to antibiotics.

Although antibiotics are useful for treating infections, their use can be accompanied by concentration-dependent toxicity and side effects. It is, therefore, important to ensure that their plasma concentrations do not exceed toxic levels. It is equally important to ensure that fear of toxicity does not result in a therapeutically inadequate dosage.

The encapsulation of antibiotics into liposomal formulations has been described (Lagacé et al., 1991, J. Microencapsulation 8:53–61; Boswell et al., J. Clinical Pharmacology 38:583–592 and references therein; Da Cruz et al., 1993, WO 93/23015 and Proffitt et al., 1994, WO 94/12155). Nevertheless, these formulations fail to display a very drastic enhancement of the therapeutic activity of the antibiotic as compared to its activity in the free form. Indeed, the preferred aminoglycoside (netilmicin) liposomal formulation of Da Cruz et al., which comprises phosphatidylcholine (PC), cholesterol and phosphatidylinositol (PI), only shows a modest increase activity in vivo with the aminoglycoside as part of the liposomal formulation as compared to free aminoglycoside (at best by a factor of three). Proffitt et al., disclose a different aminoglycoside (amikacin) liposomal formulation comprising PC, cholesterol and distearoyl phosphatidylglycerol (DSPG). Although the Proffitt et al., formulation appears to be superior at enhancing the in vivo therapeutic activity of the aminoglycoside as compared to that of Da Cruz, this increase is still relatively low and dependent on the tissue (10-fold in lung).

In view of the therapeutic, diagnostic, and research benefits incurring therefrom, it would be useful to have liposomes capable of fusing with pathogenic microbes and other cells.

SUMMARY OF THE INVENTION

We have now discovered that a liposomal formulation, previously known only to fuse with bacteria to deliver antimicrobials, is capable of delivering virtually any agent to a microbial cell, including a non-bacterial cell, or a macrophage. Accordingly, the invention provides compositions and methods for liposomal delivery of compounds to cells.

In the first aspect, the invention features a low-rigidity liposomal formulation, which is characterized as being free of cholesterol, and including neutral and anionic phospholipids at a molar ratio of 5:1 to 20:1, having a phase transition temperature ($T_c$) below 42° C. as measured by differential scanning calorimetry (DSC), where said $T_c$ is below about 42° C., such that the formulation enhances fusion of the neutral and anionic phospholipids with a cell, where the formulation either does not include an antibacterial compound or where the formulation does not enhance penetration inside a bacterial cell.

In preferred embodiments of the first aspect, the formulation further comprises an agent, preferably an antimicrobial agent. In other preferred embodiments the cell is a macrophage or a non-bacterial microbial cell, preferably a fungus (e.g. a yeast), or the agent to be delivered is not an antimicrobial agent, for example, a nucleic acid encoding a commercially useful protein.

In other embodiments of the invention, the neutral and anionic phospholipids are present at ratios of about 8:1 to 18:1 or 10:1 to 15:1. The preferred neutral phospholipid may be dipalmitoylphosphatidylcholine (DPPC) or 1,2-di-o-hexadecyl-sn-glycero-3-phosphocholine (DHPC) and the preferred anionic phospholipid may be dimirystoylphosphatidylglycerol (DMPG) or soybean 1-α-phosphatidylinositol (PI).

In other embodiments of the invention, the formulation may comprise two or more agents with different mechanisms of actions. In other embodiments of the invention, the agent may be an antibiotic, such as tobramycin or amphotericin B; a fungicide (preferably a fungicide that is not an antibacterial compound); a detergent; a nucleic acid, such as an antisense oligonucleotide or a nucleic acid encoding a cytotoxin; or a compound, such as a dye. The concentration of tobramycin or amphotericin B may range from 0.1 ug/ml to 500 mg/ml, preferably from 1 ug/ml to 50 mg/ml.

A second aspect of the invention provides a method of killing non-bacterial microbes. In preferred embodiments, the method includes treating, prevention, or diagnosis of a non-bacterial microbial infection in a mammal, comprising administration of a pharmaceutically effective amount of the liposomal formulation of the invention to the mammal. A related aspect of the invention provides a method of killing a microbe ex vivo, comprising administration of a pharmaceutically effective amount of the liposomal formulation of the invention to the microbe. In a preferred embodiment of this aspect, the microbe is in a cell culture medium.

A third aspect of the invention provides a method of treating a mammal, comprising administration of a pharmaceutically effective amount of the liposomal formulation to the mammal. The invention also provides a method of preventing a microbial infection, for example, a bacterial infection, in a mammal, comprising comprising administration of a pharmaceutically effective amount of the liposomal formulation of the invention to the mammal. In an embodiment of this aspect, the bacteria may be *Pseudomonas aeruginosa, Burkholderia cepacia, Escherichia coli,* and *Staphylococcus aureus,* and the mammal may be a human with cystic fibrosis or chronic infection. In another embodiment of this aspect, the formulation enhances penetration, by direct interaction with a microbe, of the agent through at least one of the microbial outer membrane and exopolysaccharide layer. Hence, the liposomal formulation of the present invention may provide increased efficacy in the prevention of mucoid bacterial infection, as is the case with, for example, bovine mastitis.

A fourth aspect of the invention provides method of diagnosing a microbial infection in a mammal, comprising administration of a pharmaceutically effective amount of the liposomal formulation, and an agent, to the mammal. In a preferred embodiment of this aspect, the agent is a dye.

A fifth aspect of the invention provides a method of delivering an agent inside a macrophage, comprising administration of the liposomal formulation of the invention to the macrophage.

A sixth aspect of the invention provides a method of delivering an agent inside a cell, comprising administration of the liposomal formulation of the invention to the cell.

In various embodiments of the above aspects, the mammal is a human and the administration is systemic, for example, for the treatment of septicemia. In an embodiment of these aspects, the infection is caused by at least one type of fungus, preferably a yeast, such as Candida, Histoplasma, Blastomyces, Coccidioides, Aspergillus, Mucomycosis, Microsporum, Epidermophyton, Trichophyton, and Cryptococcus species. In another embodiment, the infection is a respiratory infection, i.e. in an immunocompromised patient, and the yeast is Candida or *Aspergillus fumigatus.* In other embodiments, the microbial infection is *Pneumocystis carinii* pneumonia (PCP) and the formulation further includes pentamidine, a drug which is used for the prevention and treatment of PCP.

A seventh aspect of the invention provides a method of treating a drug-resistant microbial infection in a mammal, comprising administration of a pharmaceutically effective amount of the liposomal formulation of the invention to the mammal. In preferred embodiments of this aspect of the invention, the drug-resistant microbial infection is a bacterial infection or a yeast infection.

An eighth aspect of the invention provides a method of preventing proliferation of a drug-resistant microbe in a mammal, comprising the administration of a pharmaceutically effective amount of the liposomal formulation to the mammal.

A ninth aspect of the invention provides a use of the liposomal formulation for the treatment or prevention of a microbial infection in a mammal.

A tenth aspect of the invention provides a use of the liposomal formulation for the manufacture of a medicament for treating or preventing a microbial infection in a mammal.

An eleventh aspect of the invention provides a method of making the liposomal formulation, comprising mixing the neutral and anionic phospholipids in a solution; evaporating the solution to form a lipid film; hydrating the lipid film; extruding the hydrated lipid film through a suitable porous material; where the method lacks a lyophilization step.

By "free of cholesterol" is meant a formulation that is lacking cholesterol sufficient to alter the stability of the liposomal formulation such that the $T_c$ is increased by greater than 5% compared to a formulation without any cholesterol.

By "phase transition temperature" or "$T_c$" is meant the temperature at which liposomes destabilize or go into liquid phase, as measured by differential scanning calorimetry (DSC) or nuclear magnetic resonance (NMR). For the purposes of this invention, the $T_c$ of the liposomes of the invention is destabilization above 35° C. and liquid phase below 40° C. as measured by NMR, or destabilization above 29° C. and liquid phase below 42° C., as measured by DSC. Preferably, the $T_c$, as measured by destabilization by DSC, is about 37° C. or below the body temperature of the animal to be treated.

By "enhances fusion" is meant any increase in fusion of the liposomes of the invention with a cell when compared with liposomes that have a significant amount of cholesterol or other stabilizing agent.

By "enhance penetration" is meant any increase in the penetration or delivery of an agent inside a cell by enhanced fusion of the cell with the liposomes of the invention.

By "agent" is meant any compound or chemical, be it naturally-occurring or artificially-derived. The term agent is designed to include, but is not limited to antibiotics, fungicides, detergents, bioactive molecules, such as proteins or parts thereof, nucleic acids or part thereof, amino acid analogs or nucleoside analogs, contrast and diagnostic materials (e.g. dyes), cytotoxins, growth factors, hormones, such as corticosteroids, or components thereof. The term agent includes a combination of more than one agent.

By "antimicrobial agent" is meant any agent that is capable of causing death or preventing proliferation of a microbe.

By "drug-resistant" is meant any microbe that is capable of surviving what was previously determined to be lethal concentrations of an agent.

By "pharmaceutically effective amount" is meant an amount of an agent sufficient to produce a healing, curative, or ameliorative effect in the treatment or prevention of a microbial infection.

Other features and advantages of the invention will be apparent from the detailed description of the preferred embodiments given hereinafter. However, it should be understood that the detailed description, while indicating preferred embodiments of the invention, are given by way of illustration only, since various changes and modifications within the spirit and scope of the invention will become apparent to those skilled in the art.

DETAILED DESCRIPTION OF THE INVENTION

This invention provides a low-rigidity liposomal formulation which is capable of encapsulating an agent, fusing with microbes, and being engulfed by macrophages. The low-rigidity liposomal formulation allows for increased penetration of an agent into microbial cells, including non-bacterial cells. The present invention also provides a liposomal formulation which permits a modulated release of the agent over time and hence permits a well-controlled release of the agent. The formulations of the invention include formulations that increase the microbicidal activity of an agent, relative to free agent. In addition, the invention also provides an antimicrobial liposomal formulation effective against microbial strains having significant variations in their external membrane and/or cell wall composition. Thus the liposomal formulation permits an increase in the penetration of the agent through the outer membrane and mucoid exopolysaccharides such as those secreted by mucoid variants of bacteria.

The present invention provides pharmaceutical or veterinary uses of the liposomal formulations in the treatment or prophylaxis of microbial infections. Both chronic and acute microbial infections are included in the invention. This aspect of the invention has particular significance for those individuals who are susceptible to opportunistic microbial infections. These include those who are chronically ill, immunocompromised, pregnant, diabetic, or suffer from liver disease or alcoholism. Immunocompromised individuals include patients with lymphoma, leukemia, or AIDS, and those taking immunosuppressive medication, such as organ transplant patients.

The present invention also provides a liposomal formulation that could serve as a diagnostic or research tool. Numerous types of bioactive, agents could be coupled to the liposomes of the invention, for example antibodies, in order to target a specific tissue or cell type. The detection of the target can be assessed according to known methods, including for example the use of a label, radioactive or not, or a dye entrapped of the liposomes. One of numerous examples of the diagnostic use of the liposomal formulations of the invention is to target a tumoral antigen, through an antibody specific to this antigen, in order to detect, quantify or analyze the presence of metastases. The liposomal/antibiotic formulations of the invention may be targeted with monoclonal antibodies or other molecules to a particular tissue or cell, such as a yeast or a macrophage.

The agent is preferably an antibiotic, but other non-antibiotic agents are also included in the scope of the present invention. Two or more agents with different mechanisms of action may also be delivered using the liposomal formulation. Thus, this includes the potential for synergy among different agent combinations. The present invention further provides liposomal aminoglycoside or β-lactam formulations, preferably containing tobramycin, or fungicide formulations, preferably containing Amphotericin B.

The agent selected will depend upon the organism causing the infection. Antibiotics can be subdivided in different groups which include, among others, the β-lactams, aminoglycosides, macrolides, lincomycin, clindamycin, tetracyclines, chloramphenicol, vancomycin, rifampin, quinolones, polyenes and sulfonamides. Suitable antibiotics include but are not limited to: penicillin, ampicillin, netacillin, carbencillin, tetracycline, tetracycline hydrochloride, oxtetracycline hydrochloride, chlortetracycline hydrochloride, 7-chloro-6-dimethyltetracycline, doxycycline, doxycycline monohydrate, methacycline hydrochloride, minocycline hydrochloride, rolitetracycline, dihydrostreptomycin, streptomycin, gentamicin, kanamycin, neomycin, erythromycin, carbomycin, oleandomycin, troleandomycin, Polymysin B, collistin, cephalothin sodium, cephaloridine, cephaloglycin dehydrate, cephalexin monohydrate, amphotericin B, fluconazole, miconazole, clotrimazole, and ketoconazole.

A potent agent may include, among others, a nucleic acid encoding a cytotoxin. Where a nucleic acid is being delivered according to the invention, it generally includes a nucleic acid sequence which encodes a therapeutic substance, for example, a proteinaceous toxin, e.g., ricin, or diphtheria toxin, which, when delivered to the cells, causes cell death. Such toxin-encoding nucleic acids are also used where the invention is employed to enhance dispersion of cancer-fighting cytotoxins.

The term lipid is designed to include, but is not limited to, saturated lipids, non-saturated lipids, synthetic lipids or lipids derived from natural sources, provided that the lipid-agent composition displays fluidity/stability which is compatible with fusion to a microbial cell and/or its modulated release. Lipids may include suitable phosphatidylcholines, phosphatidylglycerols, or other lipids include those obtained from soy, egg or plant sources or those that are partially or wholly synthetic. Preferred lipids are: dipalmitoylphosphatidylcholine (DPPC), 1,2-di-o-hexadecyl-sn-glycero-3-phosphocholine (DHPC), soybean 1-α-phosphatidylinositol (PI) and dimirystoylphosphatidylglycerol (DMPG).

The term microbial infections includes, but is not limited to, Gram negative bacteria, such as genera Salmonella or Pseudomonas, Gram positive bacteria, such as genera Mycobacteria, as yeast, such as genera Candida, Histoplasma, Blastomyces, Coccidioides, Aspergillus, Mucomycosis, Microsporum, Epidermophyton, Trichophyton, and Cryptococcus.

Depending upon the purpose of delivery, the liposomal formulation may be administered by a number of routes: in humans and animals these include but are not limited to injection (e.g., intravenous, intraperitoneal, intramuscular, subcutaneous, intraauricular, inflamammary, intraurethral, etc.), topical application (e.g., on afflicted areas), and by absorption through epithelial or mucocutaneous linings (e.g., ocular epithelia, oral mucosa, rectal and vaginal epithelial linings, the respiratory tract linings, nasopharyngeal mucosa, intestinal mucosa, etc.).

The mode of administration of the preparation may determine the sites and cells in the organism to which the compound will be delivered. If the site of infection or affliction is external or accessible the liposome-entrapped agent can be applied topically. Liposomes may be administered alone but will generally be administered in admixture with a pharmaceutical carrier selected with regard to the intended route of administration and standard pharmaceutical practice. The preparations may be injected parenterally, for example, intraperitoneally, intra-arterially or intravenously. The preparations may also be administered via oral, subcutaneous, intramuscular and, of course, intramammary routes. For parenteral administration, they can be used, for example, in the form of a sterile aqueous solution which may contain other solutes, for example, enough salts or glucose to make the solution isotonic. Other uses, depending upon the particular properties of the preparation, may be envisioned by those skilled in the art. Delivery of the liposomal formulation by way of a aerosol is also contemplated as a preferred method of administration. For example, but not limited thereto, the formulations of the present invention could be used in the treatment of respiratory diseases. Asthma or yeast respiratory infections are two of the numerous diseases for which these formulations cold be used.

For administration to animals, including humans, for the curative treatment or prophylaxis of disease states, the prescribing medical professional will ultimately determine the appropriate dosage for a given subject, and this can be expected to vary according to the agent, weight, and response of the animal as well as the nature and severity of the disease, and whether the disease is acute or chronic. The dosage of agent in liposomal form can, according to the present invention, be lower than that employed for the free agent. In some cases, however, it may be necessary to administer equal or higher doses. It is also contemplated that periodic treatments or different cycles of treatment might be beneficial.

The route of delivery of liposomes can also affect their distribution in the body. Passive delivery of liposomes involves the use of various routes of administration, e.g., intravenous, subcutaneous and topical. Each route produces differences in localization of the liposomes. Two common methods used to actively direct the liposomes to selected target areas are binding, for example, either antibodies or specific receptor ligands to the surface of the liposomes. Antibodies are known to have a high specificity for their corresponding antigen and have been shown to be capable of being bound to the surface of liposomes, thus increasing the target specificity of the liposome-encapsulated drug.

Depending on the desired application, the purpose of delivery, the route of delivery, the target, and other parameters relating to the use of the formulation, the size of the liposomes can be adapted according to well known methods. For example, it is well known that large liposomes are better suited for a topical application while smaller liposomes are preferred for intravenous administration. Further, the size of the liposomes affect their capacity to be phagocytized by macrophages. Thus, the size of the liposomes can be adapted in order to favor a route of administration, to favor retention in the reticulo-endothelial organs or to favor phagocytosis (to treat bacteria inside the macrophage for example). The sizes of the liposomes contemplated range from the nanometer to the micron, preferably between 100 nm to 1 $\mu$m. In a preferred embodiment the size of the liposomes range between approximately 200 nm to 600 nm. Such a liposomal formulation is compatible with an aerosol administration of the formulation for delivery to the lungs of an animal.

A preferred formulation includes liposomes comprising an encapsulated agent where the liposomes are multilamellar vesicles having an average size ranging between 0.2 $\mu$m and 0.6 $\mu$m. The molar amount of negatively charged lipid is typically 6.5% to 11% of total lipid, and the encapsulation efficiency is typically greater than 20%. A preferred ratio of neutral to anionic lipid is about 5:1 to 20:1 and a preferred agent to total lipid ratio is from about 1:1 to 1:10. Other preferred formulations include suitable lipids like phosphatidylcholines, phosphatidylinositols, and/or phosphatidylglycerols present individually or in mixture, in a molar ratio ranging from about 0.01 to 20. Other preferred formulations include formulations where the agent to total lipid ratio is from 1:10 to 1:1.

In addition, before achieving the formulations of the invention, a great number of formulations generally described in WO 93/23015, WO 94/12155, U.S. Pat. No. 4,235,871 and U.S. Pat. No. 4,981,692 were prepared. These include DSPC:DMPG, DSPC:DPPC, DPPC:DMPC, in a molar ratio of 15:1 and 10:1, with or without cholesterol (at a molar ratio of 1, ie: 10:1:1). None of these formulations, also comprising tobramycin, showed a marked improvement of antibacterial activity when compared to free tobramycin. Furthermore, these experiments suggested that the presence of cholesterol improves liposomal stability in a way that goes against the desired antimicrobial activity of the formulation.

Based on physico-chemical properties of phospholipids, many new liposomal formulations were designed in order to promote the in vivo microbicidal efficacy of the agent while maintaining encapsulation efficiency, prolonged residence time in targeted organ, and low toxicity. Those new liposomal formulations were submitted to different in vitro and in vivo tests.

According to the present invention, the method of preparation of the multilamellar liposomes can be divided into 5 major steps (Lagacé et al., 1996, WO 96/19972; Lagacé et al., 1997, U.S. Pat. No. 5,662,929). Lipids are dissolved in chloroform (about 1 mg lipid/ml chloroform or more) and the solution is evaporated to form a lipid film between room temperature and 60° C. The lipid mix is preferably negatively charged and the resulting lipid concentration ranges from about 5 mM up to 130 mM. The liposomal preparations are typically mixtures of two components or more: a phosphatidylcholine and a negatively charged molecule such as a phosphatidylglycerol with each component of the liposomal preparation in molar ratios of 40–90% and 5–60%, respectively. A preferred combination is DPPC:DMPG at a ratio of 10:1 to 15:1, with the total lipid concentration ranging from 5 to 85 mM. The resultant negatively charged lipid induces high agent encapsulation efficiencies while the lipidic formulation promotes increased penetration of antibiotics in microbial cells. The lipidic film is hydrated with phosphate buffered saline (PBS) diluted 1:20. In an embodiment of the invention, the liposomal formulation may contain a agent. In this event, the lipidic film is hydrated with an aqueous solution of the agent.

Following hydration of the lipid film and formation of multilamellar liposomes, the preparation is subjected to freezing either in liquid nitrogen (−170° C.) or for two hours in a deep freezer (−70° C.), followed by lyophilization in a freeze dryer at 5 mtorr for 24 hours. Lyophilized samples are conserved at −70° C. or −20° C. until use. For utilization, the lyophilized powder is rehydrated with a solution of the agent (10 mg/ml to 40 mg/ml) at ⅛ portion of the initial volume with vigorous vortexing followed by incubation at 65° C. for 60 minutes, vortexing every 10 minutes. The suspension is then brought up to 50% of the initial volume with a buffered saline solution and vigorously vortexed again. Preferably, multilamellar vesicles are extruded through successively smaller-pore polycarbonate membranes ranging from 1 μm down to 0.2 μm, or as desired, to achieve a gradual reduction in liposome size. Finally, the sized mixture is centrifuged two times, for 20 minutes at 5,000 g and the pellet resuspended in saline solution.

The multilamellar liposomes may be prepared using an alternate "liquid" method. The lipids are dissolved in chloroform or a mixture of chloroform/water/methanol and the solution is evaporated to form a lipid film as described above. The lipid film is hydrated and multilamellar liposomes extruded as described above. This method specifically excludes the lyophilization step to obtain the initial liposomes.

A particularly important embodiment of the invention produces liposome/agent formulations allowing a marked increased penetration of the agent into non-bacterial cells.

EXAMPLE 1

Liposomal Formulations

Liposome formulations were prepared as described above using a variety of agents, including nucleic acids, dyes, and antibiotics, and a lipid mixture comprising dipalmitoylphosphatidylcholine (DPPC): dimirystoylphosphatidylglycerol (DMPG) at a ratio of 10:1 or 15:1, with total lipid concentration ranging from 5 to 85 mM. Hydration took place with phosphate buffered saline diluted 1:20, followed by freezing at −70° C. and lyophilization. Rehydration was done by adding a solution of the agent at ⅛ portion of the initial volume, followed by filling to 50% of the initial volume with phosphate buffered saline. Liposomes were extruded first through a 1 μm filter, followed by extrusion through 0.6 and 0.4 μm polycarbonate membranes, centrifugation two times at 5,000×g for 20 minutes, and resuspension in phosphate buffered saline.

To encapsulate nucleic acids within the liposomes of the invention, both the plasmid, pUC 18 (Yannisch-Perron. C. et al., 1985, Gene 33:103–119), and the 20 bp oligonucleotide, 5'-AATTCGAGTCAGGTCCCATG-3', were used. 250 μg of nucleic acids were rehydrated with 30 mg phospholipids, as described above. For both plasmids and oligonucleotides, 30% encapsulation was achieved, as demonstrated by agarose gel electrophoresis, followed by ethidium bromide staining of DNAase I-treated nucleic acid-encapsulated liposomes.

To encapsulate dyes within the liposomes of the invention, varying amounts of the dye, carboxyfluorescein (Molecular Probes, Eugene, Oreg.), were used. Starting amounts of 0.12 mg/ml, 0.28 mg/ml, 0.50 mg/ml, and 3.75 mg/ml of carboxyfluorescein resulted in encapsulation efficiencies of 6.6%, 14.3%, 14.4%, and 32.3% of the initial quantity, respectively, as determined by optical density at 254 nm. Furthermore, fluorescence-activated cell sorting (FACS) analysis indicated that 94.6% of the liposomes showed a high level of fluorescence.

To encapsulate antibiotics within the liposomes of the invention, the aminoglycoside, tobramycin, was used in a solution of 10 mg/ml. In this embodiment the lipid mixture is dipalmitoylphosphatidylcholine (DPPC): dimirystoylphosphatidylglycerol (DMPG) at a ratio of 1:10 and 1:15, with total lipid concentration ranging from 5 to 85 mM. The final liposomal/aminoglycoside formulation had a diameter of about 0.4 μM and possessed an encapsulation efficiency of 20% and a agent/lipid ratio of 1:1. The determination of tobramycin in liposomes was performed by high-performance liquid chromatography (HPLC).

Increased rates of encapsulation may be achieved by starting with higher concentrations of tobramycin, for example, 300 mg, and using liposomes of approximately 0.4 μm size. Large quantities of tobramycin-encapsulated liposomes may be made using a lipid ratio of DPPC/DMPG of 10:1 at a total concentration of 300 mg, eliminating the concentration step, and using a total quantity of 16 g tobramycin. According to this protocol, 195 μg of tobramycin can be encapsulated per mg phospholipids at a physiological pH of 7.2. These modifications do not affect the activity of the liposomal formulation.

Other agents that may be encapsulated in liposomes include, for example, Amphotericin B, Imipinem, Pentamidine, and the nasal anti-influenza drug, A&B (Glaxo). The techniques described herein may be used to deliver two or more agents with different mechanisms of action.

EXAMPLE 2

Fusion of Liposomal Formulations with Bacteria

The formulations of liposomes were assessed for their ability to fuse with bacteria. The liposomes were prepared as described above and contained different lipid mixtures. These lipid mixtures were dipalmitoylphosphatidylcholine (DPPC): dimirystoylphosphatidylglycerol (DMPG), DPPC: soybean 1-α-phosphatidylinositol, sodium salt, (PI), and 1,2-di-o-hexadecyl-sn-glycero-3-phosphocholine (DHPC): DMPG. All lipid mixtures were used at ratios of 10:1. PI is negatively charged with a phase transition temperature ($T_c$) of 23° C., while DHPC is neutral with a $T_c$ of 42° C. All three formulations have a $T_c$ of about 29.5° C. The three formulations were used in fluorescence-activated cell sorting (FACS) studies to demonstrate the fusion of fluid liposomes with bacteria. The bacterial strain used was *Pseudomonas aeruginosa* strain 429.

To evaluate fusion of the liposomes with bacteria by flow cytometry, the liposomes were labeled with PKH2-GL using the PKH2-GL labeling kit (Sigma, St. Louis, Mich.). PHK2-GL is a probe often used to study interactions between biological membranes. This probe is a fluorescent cell linker dye containing aliphatic carbon tails which are capable of insertion into membranes. PKH2-GL possesses similar spectral characteristics as FITC, another commonly used fluorescence marker. Briefly, freeze-dried liposomes were rehydrated with phosphate buffered saline (PBS), pH 7.2. The final liposomal pellet was then used for the labeling procedure. Labeling was performed according to the manufacturer's instructions but with small modifications. A 1 ml aliquot was taken and centrifuged 30 minutes at 6000×g, 4° C. The pellet was then resuspended in 1 ml of diluant A (Sigma, St. Louis, Mich.). Diluant A is a solution contained in the kit used for the labeling procedure. Eight ml of PKH2-GL was then added for a final concentration of $4 \times 10^{-6}$ M. The volume was then brought up to 2 ml with diluant A. The PKH2-GL-liposomal solution was incubated for 5 minutes at room temperature with circular agitation. Following the incubation, 2 ml of bovine serum albumin at 1% (w/v) in PBS was added and the solution was further incubated for 1 minute with agitation to stop the labeling reaction. The PKH2-GL-liposomes were then washed twice with PBS by centrifuging at 5000×g, 30 minutes, 4° C. to remove any free PKH2-GL. Labeling efficiency was on average 95% as determined by flow cytometric analysis.

Integration of the PKH2-GL-liposomes to bacterial cells was demonstrated by fluorescence-activated cell sorting (FACS) analysis. *P. aeruginosa* 429 or ATCC 25619 were incubated for 17 hours in proteose peptone broth no 2. A solution of 0.3 of O.D. (660 nm) was then made. The solution was centrifuged and the cell pellet resuspended in RPMI supplemented with 2.5% fetal calf serum for washing. The final cell pellet was resuspended in RPMI supplemented with 2.5% fetal calf serum to obtain the same initial concentration. RPMI was used because it was determined to be the best medium for reducing background fluorescence of *P. aeruginosa* due to siderophore production. Aliquots of 18 ml were then taken and transferred to conical tubes of 50 ml (Sarstedt, St-Laurent, Québec, Canada). Bacteria were incubated either with 200 ml of liposomes labeled with PHK2-GL, 200 ml of PBS (negative control) or 80 ml of free PKH-2GL (positive control) to obtain a final concentration of $4 \times 10^{-6}$ M. PBS was then added to complete the volume to 20 ml and the tubes were incubated at 37° C. with agitation (250 RPM). Two ml samples were taken after 10 minutes, 0.5, 1, 2, 3, 4, 5 and 6 hours of incubation. The liposomes and free PKH2-GL were separated from the bacteria by centrifugation through a sucrose of 21% (w/v) in PBS. The recovered bacterial pellet was washed twice in PBS and the final cell pellet was fixed with 300 ml of 2% paraformaldehyde diluted in PBS for FACS analysis.

All experiments were done in duplicate and the results averaged. The time needed to reach the maximal fusion rate was 3–4 hours. The results were expressed as a percentage of bacteria showing PKH2-GL fluorescence relative to the total number of bacteria. A total of 10,000 events per 10 seconds were enumerated. The results shown in Table 1 indicate a significant integration or fusion of liposomes-PKH2-GL with bacteria *P. aeruginosa* 429, indicating that different combinations of neutral and anionic phospholipids are very effective in fusing with microbial cell membranes.

TABLE 1

Fusion of Liposomes-PKH2-GL with *Pseudomonas Aeruginosa* 429

| Time (h) | DPPC/DMPG | DPPC/PI | DHPC/DMPG |
|---|---|---|---|
| 0 | 2.88 | 2.13 | 5.34 |
| 0.5 | 3.50 | 5.69 | 6.26 |
| 1 | 5.56 | 3.45 | 5.74 |
| 2 | 8.52 | 23.91 | 16.00 |
| 3 | 33.17 | 37.47 | 33.74 |
| 4 | 28.37 | 31.06 | 25.6 |
| 5 | 11.35 | 12.4 | 18.48 |
| 6 | 6.71 | 9.17 | 8.6 |

EXAMPLE 3

Physical and Biological Characteristics of Tobramycin-Liposomal Formulations

Different tobramycin-encapsulated liposomal formulations were prepared according to Example 1 and analyzed by differential scan colorimetry. Using differential scan calorimetry, the temperatures of phase transition ($T_C$) were calculated for the tobramycin-liposomal formulations listed in Table 2. All these formulations were then listed in vitro to assess the antibiotic kinetics of liberation from the liposomes. In addition, these formulations were tested in a non-infected mouse model as previously described (Omri et al. 1994, Antimicrob. Agents Chemother. 38:1090–1095) to assess the persistence of the liposomes in the lung. Only the DPPC/DMPG 10:1, 15:1 and DSPC (Disteroylphosphatidylcholine)/DMPC (dimirystoyl-phosphatidylcholine) 15:1 liposomal formulations (shown in Table 2) exhibited the following characteristics: liberation of gradual and convenient amounts of antibiotic by virtue of their fluidity/stability characteristics.

These liposomal formulations were further tested in animal model of chronic pulmonary infection to examine their antibacterial efficacy. Contrary to the two DPPC/DMPG formulations, the DSPC/DMPC formulation was shown to be inactive in this animal model. In addition, some formulations displaying a phase transition temperature comparable to that of the two DPPC/DMPG formulations, although showing the desired fluidity/stability characteristics, were shown to be inefficient in the uninfected animal model. Of note, the addition of cholesterol to the formulation described in Table 2 brought the $T_c$ to a minimum value of 60° C. Such formulations were incompatible with modulation of gradual antibiotic liberation and suitable interactions with microbes.

Thus, in order to maintain the desired characteristic of the liposome formulation, a low-rigidity of the liposomes seems required. This low-rigidity can be achieved by maintaining a low temperature of phase transition (under 40° C.) and avoiding the use of cholesterol in the formulation.

TABLE 2

| Phospholipids | ratio | Destablization Temperature |
|---|---|---|
| DSPC/DMPG | 15:1 | 44 |
| DSPC/DMPC | 15:1 | 42 |
| DSPC/DPPC | 15:1 | 46 |
| DSPC/DMPG | 10:1 | 40 |
| DSPC/DMPC | 10:1 | 42 |
| DSPC/DPPG | 10:1 | 45 |
| DPPC/DMPG | 10:1 | 29.5 |
| DPPC/DMPG | 15:1 | 35 |

To further understand the fusion mechanism between the liposomes and bacterial cell membranes, the effect of pre-administering the liposomes may be measured relative to the efficacy of tobramycin on tobramycin-sensitive *P. aeruginosa*. This may be done by determining the rate of replication of microorganisms after fusion. The uptake of Imipenem, for example, may be also be measured in specific microbes such as *P. aeruginosa, B. cepacia,* and Xanthomonas. Other physical parameters of the liposomes, such as the relationship of size of the liposomes relative to various modes of treatment, may be assessed by a variety of techniques, including electron microscopy.

EXAMPLE 4
Pulmonary Retention of the Agent

Studies of pulmonary retention were done with liposomes prepared with a 10:1 molar ratio of DPPC:DMPG, as prepared in Example 1, in BALB/c mice (Charles River), and using free tobramycin as control. The animals were injected intracheally as previously described (Omri et al., 1994, Antimicrob. Agents Chemother. 38:1090–1095) with one dose of 50 µl (200 µg) of the free and liposomal tobramycin preparations and lungs, kidneys and blood were collected at fixed times (Table 3). Lungs and kidneys were removed aseptically, weighed, and then homogenized in cold sterile PBS (40% [wt/vol]) for 30 s with a Polytron homogenizer. Tobramycin levels in both homogenized tissues and sera were measured by HPLC. Groups of three mice were used for each time value.

formulation shown in Table 2. This result is in contrast to that of a DSPC:DMPG (10:1) formulation which showed a constant concentration of tobramycin over time, and hence a high stability of the liposomes (Ormi et al., 1994, Antimicrob. Agents Chemother. 38: 1090–1095, also see below).

EXAMPLE 5
In Vivo Analysis of the Bactericidal Activity of Tobramycin-Encapsulated Liposomes To evaluate the bactericidal efficacy of a liposomal aminoglycoside formulation produced according to the present invention, male, pathogen-free, Sprague-Dawley rats weighing 175 to 225 g (Charles River) were used. Chronic infection in lungs was established by intratracheal administration of $5 \times 10^5$ CFU of *Pseudomonas aeruginosa* PA 508 (mucoid phenotype) prepared in agar beads.

After 3 days, three doses (600 µg) of free or liposome-encapsulated tobramycin were given intratracheally at intervals of 16 h. The lipid mixture were DPPC:DMPG at a molar ratio of 10:1 (formula no 1) and DPPC:DMPC at a molar ration of 15:1 (formula no 2). Sixteen hours after the last treatment, the animals were sacrificed and the entire lungs were removed aseptically, weighed, and homogeneized as described previously for mice. Serial 10-fold dilutions of the homogenates in cold PBS were made and spread in triplicate

TABLE 3

Comparative antibiotic concentrations following administration of free and liposome-encapsulated tobramycin in mice

| Time (h) | Conc. (ug/pair of lungs) | | Conc. (ug/pair of kidneys) | | Sera (ug/ml) | |
|---|---|---|---|---|---|---|
| | Free tobramycin | Liposomes | Free tobramycin | Liposomes | Free tobramycin | Liposomes |
| 0.25 | 43 | 58 | ND* | ND | ND | ND |
| 1 | 11 | 27 | 25 | 19 | UD† | 5 |
| 8 | UD | 46 | ND | ND | ND | ND |
| 24 | UD | 73 | ND | ND | ND | ND |
| 32 | UD | 17 | ND | ND | ND | ND |
| 48 | UD | 15 | UD | 13 | UD | UD |

*ND: not done; †UD: undetectable

Administration of the liposomal aminoglycoside formulation, prepared according to this invention, resulted in a prolonged pulmonary retention time of the encapsulated form of tobramycin in lungs compared with that of the free agent. It is to be noted, however, that the concentration of tobramycin decreases with time with the DPPC:DMPG on proteose peptone agar plates. Identification of *P. aeruginosa* was confirmed by specific cultures. CFU were counted after 24 hour incubations at 37° C. under 5% $CO^2$. Counts were expressed in log CFU per pair of lungs. PBS and PBS-liposomes were used as controls. The results are listed in Table 4.

TABLE 4

Bactericidal effect of liposomal tobramycin on *P. aeruginosa* in infected rat lung tissues

| Regimen | # rats | cfu/pair of lungs | log cfu/pair of lungs |
|---|---|---|---|
| PBS only | 2 | $1.40 \times 10^6$ | 6.15 |
| Liposome-PBS (formula no. 1‡) without tobramycin | 2 | $2.32 \times 10^7$ | 7.36 |
| Liposome-tobramycin (formula no. 1‡) | 5 | <significant count* | <significant count* |
| Liposome-PBS (formula no. 2‡) | 3 | $2.11 \times 10^7$ | 7.32 |

TABLE 4-continued

Bactericidal effect of liposomal tobramycin on P. aeruginosa in infected rat lung tissues

| Regimen | # rats | cfu/pair of lungs | log cfu/pair of lungs |
|---|---|---|---|
| Liposome-tobramycin (formula no. 2‡) | 6 | $1.83 \times 10^6$ | 6.26 |
| Free tobramycin | 5 | $1.25 \times 10^7$ | 7.10 |

‡formula no. 1: formula according to the present invention used here at a molar ration 10:1, DPPC:DMPG.
*None or only rare cfu (0 to 4) were visible on plates spreaded in triplicate with undiluted lung samples. In accordance with the American Society for Microbiology, Manual of methods for general bacteriology. Washington, D.C., 1981, p. 185, cfu counts <30 are not statistically significant.
†The formula no 2 was prepared with synthetic DSPC:DMPC at a molar ratio of 15:1. This formulation like a formulation previously described (Omri et al., 1994, Antimicrob. Agents Chemother. 38:1090–1095) at 10:1 molar ratio of DSPC:DMPG represents other liposomal formulations without improved bactericidal efficacy when compared to the activity of free antibiotic agent P. aeruginosa.

A second experiment to study the bactericidal effect of the liposomal tobramycin preparation, produced according to the present invention, was carried out as for Table 4 with the following modifications: 1) liposomes were prepared with a 15:1 molar ratio of DPPC:DMPG (formula no. 3); and 2) only two doses of 240 µg of free or liposome-encapsulated tobramycin were administered to the rats. The results are shown in Table 5.

TABLE 5

Bactericidal effect of liposomal tobramycin on P. aeruginosa in infected rat lung tissues

| Regimen | # rats | cfu/pair of lungs | log cfu/pair of lungs |
|---|---|---|---|
| PBS only | 3 | $1.05 \times 10^8$ | 8.02 |
| Liposome-PBS (formula no. 3) without tobramycin | 3 | $1.24 \times 10^8$ | 8.93 |
| Liposome-tobramycin (formula no.3) | 3 | <significant count* | <significant count |
| Free tobramycin | 3 | $1.07 \times 10^6$ | 6.03 |

*None or only rare cfu (0 to 6) were visible on triplicated plates spread with undiluted lung samples.

The results of the experiments show that the in situ administration of low doses of tobramycin in lungs increases drastically the bactericidal efficacy of the encapsulated aminoglycoside comparatively to the free agent. The very strong increase of the bactericidal efficacy of the encapsulated tobramycin indicates that the liposomal formulation allows an increased diffusion across the bacterial cell membrane and intracellular accumulation of the agent. The drastic increase in antibacterial activity of relativity low doses of tobramycin as part of the liposomal formulation as compared to free, further suggests that the lipids of the formulation promote a fusion between the liposome and bacterial cells. The specific liposomal formulation prepared according to this invention presents original properties not shared by other earlier liposomal formulations. A case in point is the significant bactericidal activity of the tobramycin liposomal formulation on the mucoid P. aerguinosa strain used. Thus, the formulations of the invention appear to not only enhance the passage of the antibiotic through the outer membrane of the bacteria but also through the exopolysaccharide thereof. Thus, the present liposomal formulations can be successfully used to treat non-mucoid and mucoid forms of bacteria. The fact that low doses of aminolycosides are sufficient to present strong bactericidal efficacy reduces the toxicity of the antibacterial agent. In fact, the results in Table 4 and 5 showed a drastic bactericidal activity of the antibiotic-liposomal formulation with as little as 1.37 mg of tobramycin per kg of the animal. Previously disclosed formulations used 35–120 mg/kg of antibiotic with substantially less bacterial activity (WO94/12155 and U.S. Pat. No. 4,981,692). In addition the therapeutic liposomal formulations of the present invention are not strictly dependent on phagocytosis by macrophages as those of Popescu et al. (U.S. Pat. No. 4,981,692), designed specifically for the treatment of intracellular infections. Moreover, the fact that tobramycin concentrations observed in kidneys were lowered when encapsulated antibiotics were used comparatively to free antibiotics indicates a lowered toxicity.

The liposomal formulation may also be used in the rat agar bead model to develop a lethal infection to ensure treatment of an infected animal, rather than a colonized animal. The animal may be immunocompromised by whole body irradiation, or a P. aeruginosa lung infection may be established using the punctured lung model or by using a lung irritant.

A major issue in the treatment of diseases like cystic fibrosis (CF), for example, is managing lung congestion to help clear secretions and improve airflow and sputum clearance. Pulmozyme DNAase (Genentech) is a clinically approved therapy that has been shown to reduce the viscosity of sputum in CF patients. The bactericidal activity in the tobramycin-liposomal formulation may be compared to free tobramycin in fresh sputum. Similarly, the bactericidal activity in the sputum of patients on Pulmozyme therapy compared to those not on this therapy may be assessed to evaluate synergy between the two compounds.

This animal model may also be used to detect the presence of microbial biofilms by, for example, electron microscopy or chemical analysis.

Xanthomonas maltophilia is another type of bacteria which is very refractory to the conventional treatments. A parallel can be drawn between X. maltophilia and B. cepacia with respect to their intrinsic resistance to agents. Being relatively impermeable, infections to X. maltophilia often lead to death.

The bacterial walls of E. coli and S. aureus present very different characteristics in comparison with that of Pseudomonas. The outer membrane of Enterobacteriacae like E. coli have distinct porins and the lipoplysaccaride side chains are crosslinked, thereby conferring an unusually low permeability to the lipid bilayer region of the outer membrane to hydrophobic solutes (Nikaido, 1988, Rev. Infect. Dis. 10, Sup. 2:S279–S281). The cell wall of Gram-positive bacteria such as that of *S. aureus* consist of peptidoglycan, polysaccharides and polymers such as teichoic acids. In contradistinction to the cell walls of Gram-negative bacteria, which contain lipidic material. The porosity of the Gram-positive cell well preparations has apparently not been analysed with modem technology, but it is reasonable to assume that they are quite porous (Nikaido, 1994, J.-M. Ghuysen and R. Hakenbeck (Eds.) Bacterial Cell Wall).

Outer membrane of all species of gram-negative bacteria have been shown to contain porin channels. Hydrophilic molecules of sizes below a given exclusion limit can pass through the water-filled channels of protein called porins. In the case of aminoglycosides, a polycationic antibiotic, the mechanism of uptake across the outer membrane has been proposed to be different for *P. aeruginosa* and *E. coli*. For *P. aeruginosa*, aminoglycosides are taken up via the self-promoted uptake route (Hancock et al., 1981, Antimicrob. Agents Chemother. 19:777–785; and Nicas et al., 1980, J. Bacteriol. 143:872–878). In this pathway, the polycations act to competitively displace divalent cations which cross-bridge adjacent lipopolysaccharides (LPS) molecules, thus disrupting these important outer membrane stabilizing sites. Although this invention is not restricted to a particular theory, it is believed that this, in turn, permeablizes the outer membrane and promotes uptake of other molecules of the permeabilizing polycation. This is consistent with the polycationic nature of aminoglycosides which carry three to five positive charges. The porins of *E. coli* seem to be particularly complex since trimeric arrangements form three small pores which converge into a single water-filled channel (Engel et al., 1985, Nature (London) 317: 643–645). Two modes of aminoglycoside penetration have been suggested for *E. coli;* (1) aminoglycosides are taken up by the porin pathway; and (2) penetration of aminoglycosides may be due to aggregation-disaggregation of OmpF (porin F), mediated by interaction at a divalent cation binding site on OmpF (Hancock et al., 1991, Antimicrob. Agents Chemother. 35:1309–1314.)

The improved bactericidal efficacy in these results is related to the fact that the agent is not only incorporated into liposomes but is incorporated in a combination of phospho-lipids that markedly improves the penetration of agent in bacterial cells and through mucoid exopolysaccharides secreted by *Pseudomonas aeruginosa*.

In order to demonstrate that the liposomal formulations produced according to the present invention are effective against a wide array of bacteria strains, the bactericidal tests were performed using *P. aeruginosa*, *B. cepacia*, *E. coli*, *S. aureus* and *X. maltophilia*.

EXAMPLE 6

In Vitro Bactericidal Activity Against Different Bacterial Families

To evaluate the bactericidal efficacy of the liposonal tobramycin formulation produced according to the present invention (DPPC/DMPG), in vitro tests were performed against different clinical strains: *Pseudomonas aeruginosa* (strain 429) MIC$\geq$60 µg/ml, *Burkholderia cepacia* (strain ID-28369) MIC$\geq$27 µg/ml, *Escherichia coli* (strain 1061 mn 88) MIC$\geq$5 µg/ml, *Staphylococcus aureus* (strain LSPQ 2499) MIC$\geq$9 µg/ml and *Xanthomonas maltophilia* MIC>5 µg/ml. To culture tubes containing proteose peptone (29 ml) a minimal number of 108 CFU of bacteria in logarithmic phase (1 ml) and of one of the following preparations (100 µl) were added at time zero: free tobramycin, control liposomes or PBS. Experiments were done in triplicate. At times 1, 3, 6, and 16 hours following the addition of antibiotic or controls, 2 ml of samples were collected and serial 10-fold dilutions were made and spread in triplicate on proteose peptone agar plates for gram negative strains and on Mac-Conkey agar plates for *S. aureus*. CFU were counted after 24-hour and 48-hourS incubations at 37° C. under 5% $CO_2$. Counts were expressed in log CFU per ml of culture media. The results are presented in FIGS. 1–4 and Table 6. As it can be observed therein for all five (5) bacterial families, quantity of encapsulated tobramycin in each experiment was inferior to the MIC of the bacteria used.

TABLE 6

Viable bacterial counts (cfu) of *Xanthomonas maltophilia* in proteose peptone (MIC >5 µg/ml)

| TIME* | 0 h | 1 h | 3 h | 6 h | 16 h |
| --- | --- | --- | --- | --- | --- |
| Free tobramycin (3,12 µg/ml)** | $3.7 \times 10^{10}$ | $3.00 \times 10^{12}$ | $8.20 \times 10^{14}$ | $7.80 \times 10^{16}$ | $8.57 \times 10^{18}$ |
| Liposomes-PBS | $3.7 \times 10^{10}$ | $7.26 \times 10^{11}$ | $5.02 \times 10^{14}$ | $6.55 \times 10^{16}$ | $7.46 \times 10^{18}$ |
| PBS | $3.17 \times 10^{10}$ | $7,10 \times 10^{11}$ | $5.13 \times 10^{14}$ | $6.73 \times 10^{16}$ | $7.43 \times 10^{18}$ |
| Liposomes entrapped tobramycin (3,08 µg/ml) | $3.17 \times 10^{10}$ | $8.23 \times 10^{12}$ | $5.30 \times 10^{7}$ | $4.47 \times 10^{7}$ | $1.28 \times 10^{8}$ |

*Time of sample collections after addition of antibiotic.
**Quantity of antibiotic.

EXAMPLE 7

In vitro Fungicide Activity Against *Candida albicans*

Figure 1:
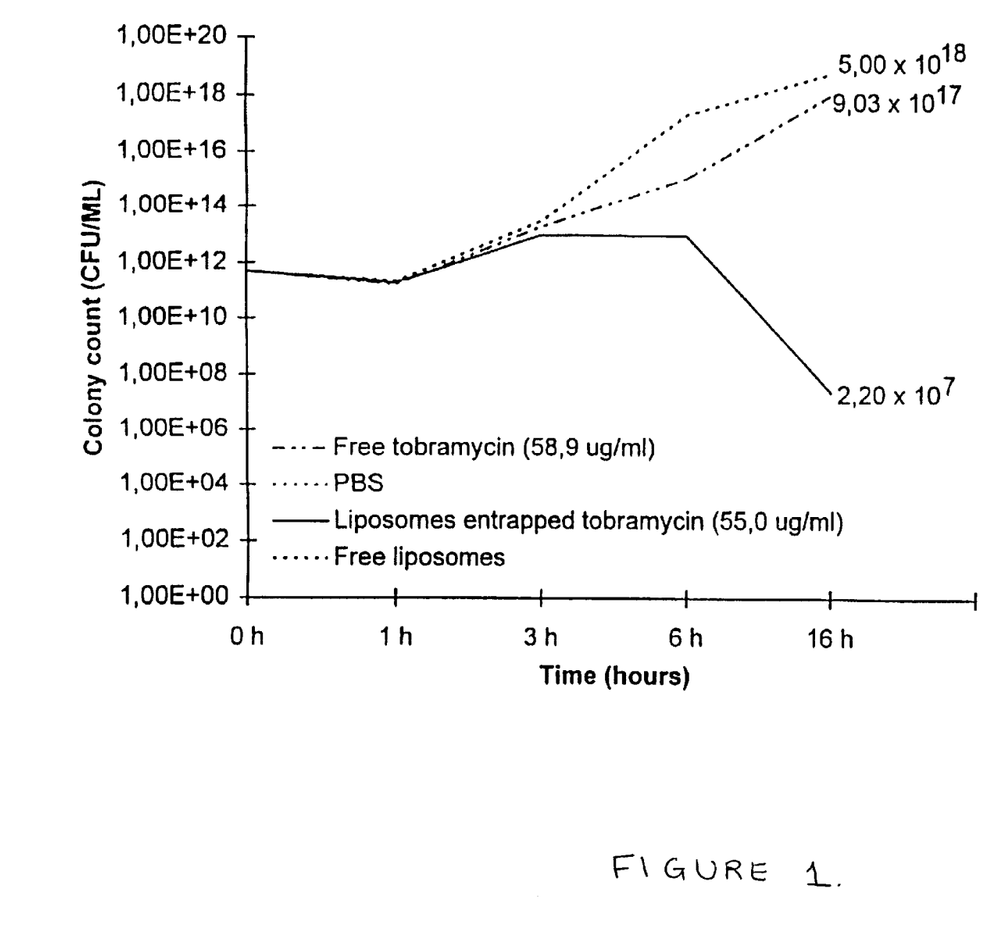
FIG. 1 shows a graphical representation of the bacterial counts of Pseudomonas aeruginosa (429) in proteose peptone (MIC>60 µg/ml) under different conditions.
Figure 2:
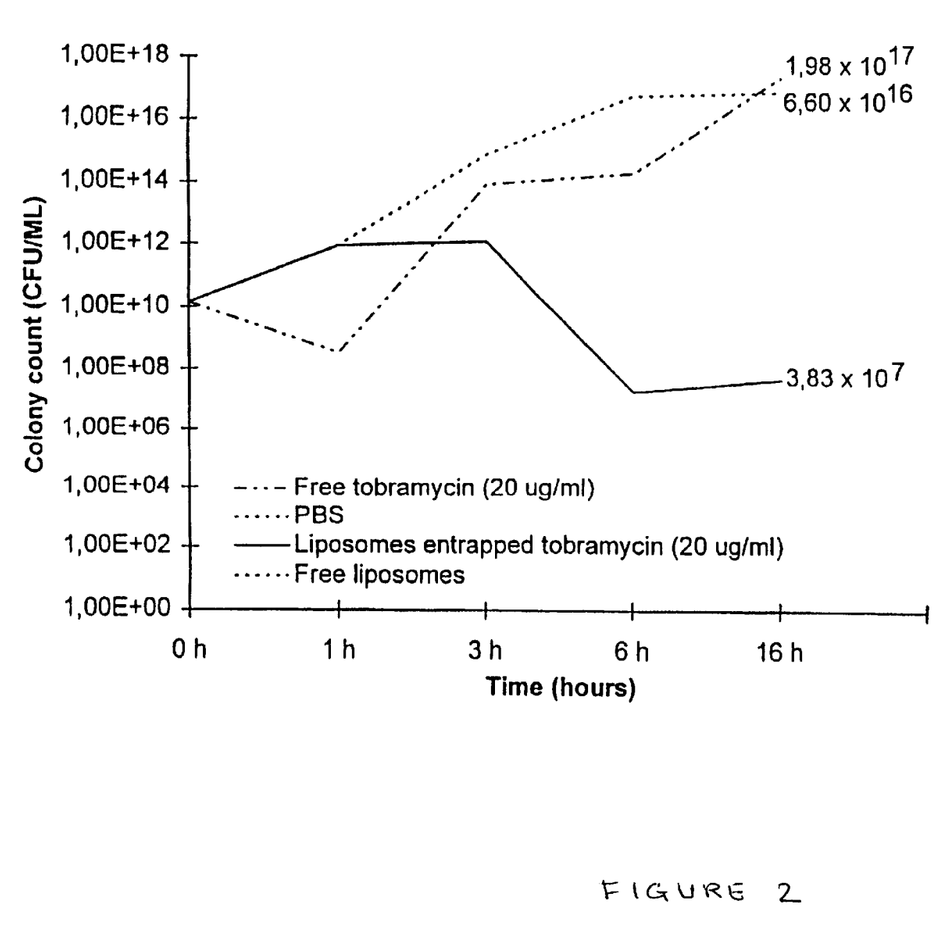
FIG. 2 shows a graphical representation of the bacterial counts of Burkholderia cepacia (LSPQ ID 28369) in proteose peptone (MIC>26 µg/ml) under different conditions.
Figure 3:
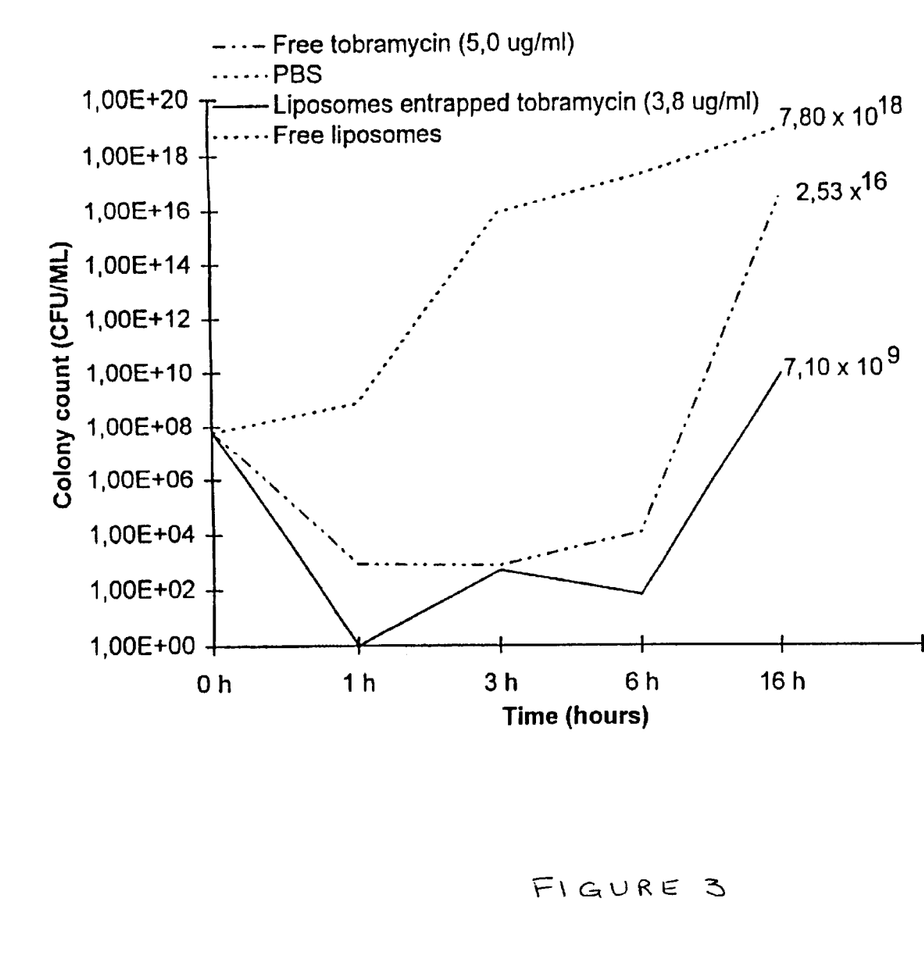
FIG. 3 shows a graphical representation of the bacterial counts of Escherichia coli (nm 88 1061) in proteose peptone (MIC>5 µg/ml) under different conditions.
Figure 4:
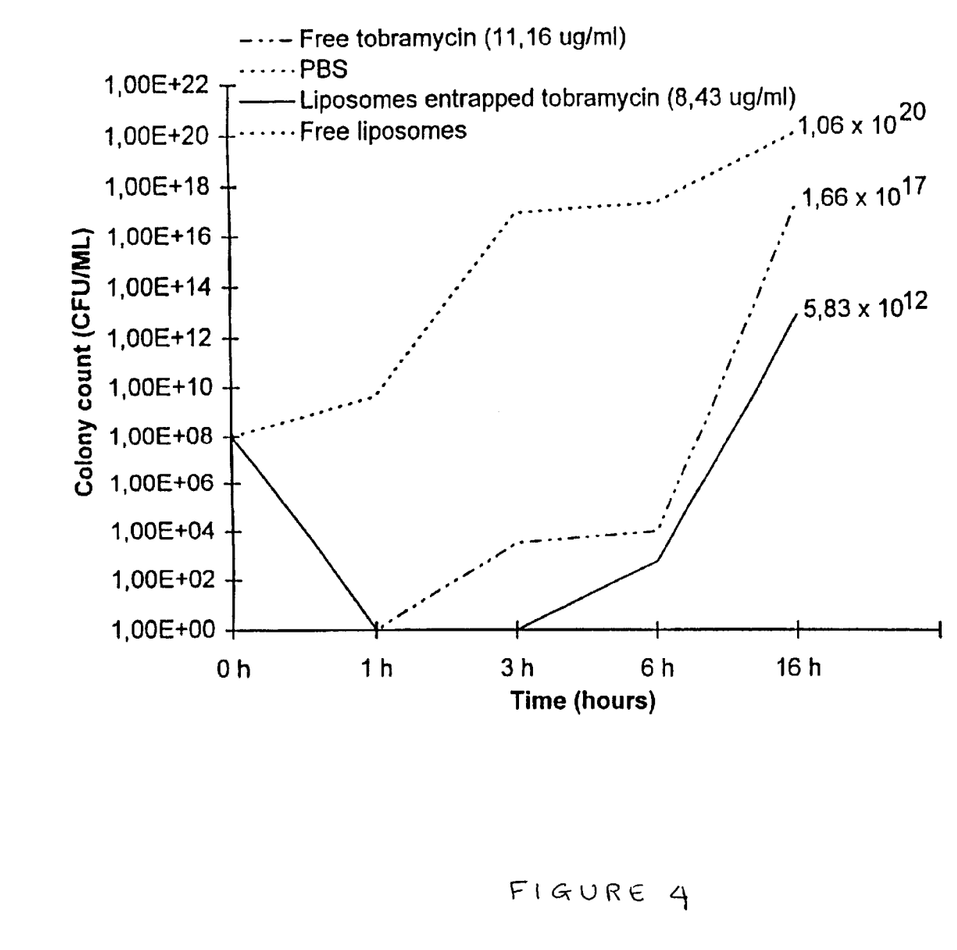
FIG. 4 shows a graphical representation of the bacterial counts of Staphylococcus aureus (LSPQ 2499) in proteose peptone (MIC>9 µg/ml) under different conditions.
Figure 5:
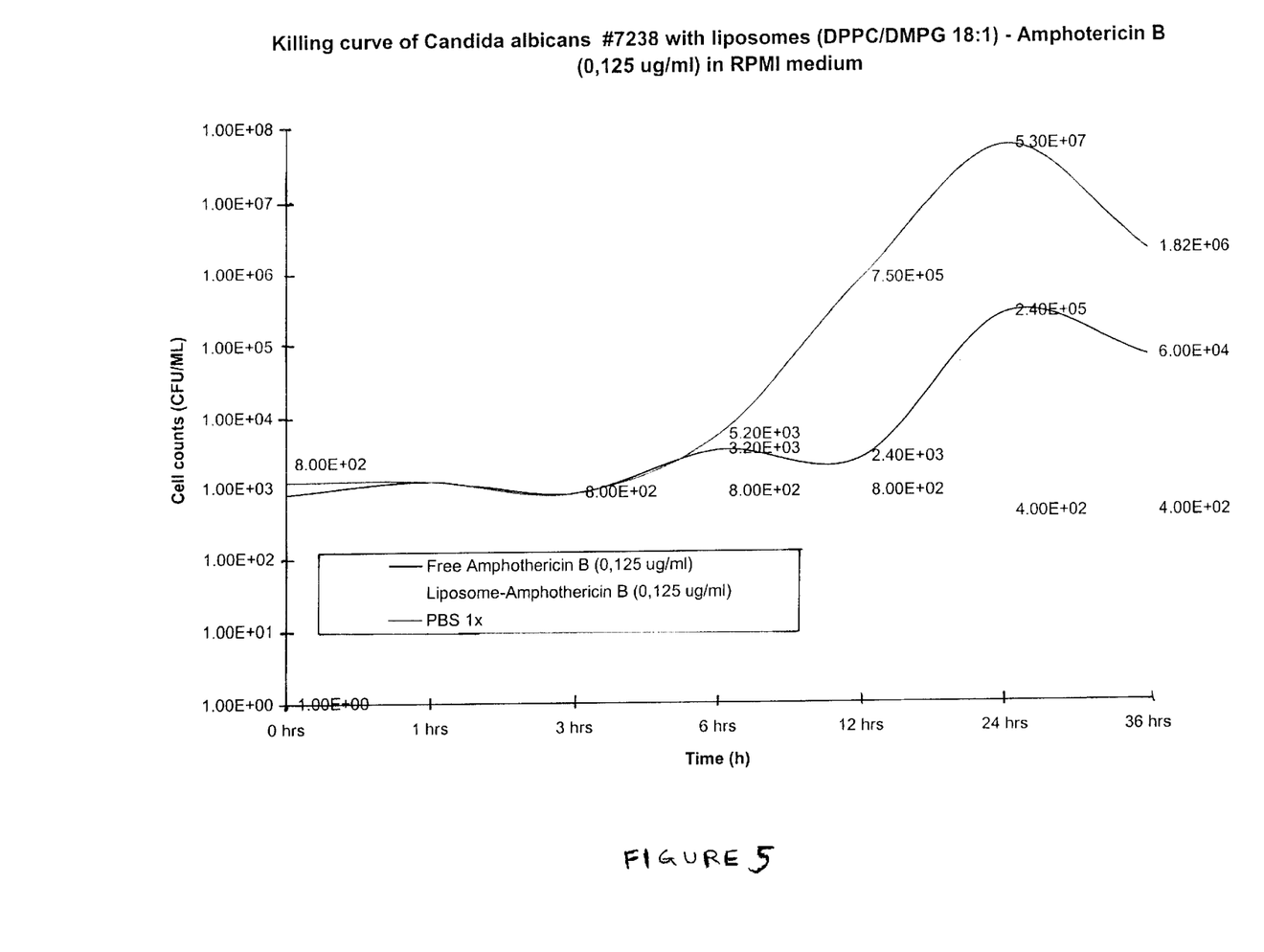
FIG. 5 shows a graphical representation of a killing curve of Candida albicans (#7238) with liposomes (DPPC:DMPG 18:1) containing Amphotericin B (0.125 µg/ml) in RPMI medium.

Yeast respiratory infections are a major problem in immunocompromised patients. To evaluate the fungicide activity of the liposomal-amphotericin B formulation produced according to the present invention (DPPC/DMPG), in vitro tests were performed against *Candida albicans*, strain 7238, MIC=1 µg/ml. To culture tubes containing 22.5 ml of *C. albicans* cells (final cell concentration of 103/ml), 7.5 ml of RPMI medium 1640 containing liposome-amphotericin B (final concentration of 0.125 µg/ml), free amphotericin B (final concentration of 0.125 µg/ml), or control PBS were added at time zero. Experiments were done in triplicate. At times 0, 3, 6, 12, 24, and 36 hours following the addition of antibiotic or control, 1.5 ml samples were collected and serial 10 fold dilutions were made and spread in triplicate on proteose peptone agar plates. CFU were counted after 24 hour and 48 hour incubations ar 37° C. under CO2. Counts were expressed in log CFU per ml of culture media. The results are presented in FIG. 5.

These methods may also be used in treating other yeast infections, such as those caused by *Aspergillus fumigatus, Histoplasma capsulatum, Blastomyces dermatitidus, Coccidioides immitis,* Histoplasma, Blastomyces, Coccidioides, Aspergillus, Candida, Mucomycosis, Microsporum, Epidermophyton, Trichophyton, and Cryptococcus.

EXAMPLE 8

Antisense Oligonucleotides withing Liposomes

Antisense techniques may be used in combination with the liposomal formulations of the present invention. Antisense oligonucleotides may be encapsulated, essentially as described above for nucleic acids. Ribosome function may be targeted as an antimicrobial strategy. Antisense sequences that bind to specific regions of 23 s ribosomal RNA may be used. These sequences are not found in mammalian cells.

Appropriate assays to monitor microbe inhibition or killing may be used. For example, % percent inhibition of transcription in at least two targets, preferably three, may be shown. These targets could include, for example, gram positive and gram negative bacteria, and yeast.

Antisense technology may be used in conjunction with liposomes using TNF-alpha as well.

EXAMPLE 9

Agents within Liposomes for Systemic Administration

Agents may be used in combination with the liposomal formulation of the invention for systemic administration. For example, the tobramycin-liposomal formulation described above may be used to determine bactericidal activity in blood. This may be done using animal models, such as rabbits, and the kinetics of free tobramycin to liposome-tobramycin may be established. Flow cytometry may be used to establish the half-life of the liposomes in blood under appropriate conditions. This approach may be used to treat blood born infections, e.g. septicemia, by systemic administration of the liposomal formulation.

EXAMPLE 10

Use of Liposomes to Overcome Microbial Drug-Resistance

Although microorganism drug-resistance has long been recognized, it continues to be an important health problem world-wide. Furthermore, based on the relative impermeability of numerous strains to antibiotics, the design of newer more efficient versions thereof, which can overcome the strain-based enzymatic degradation, still does not solve the significant hurdle of getting the antibiotic through the impermeable membrane or through an exopolysaccharide layer of the microorganism and to its site of action.

The liposomal formulation of the invention may be used, in conjunction with a agent, to provide a means to overcome microbial antibiotic resistance, such as the efflux pump mechanism. The liposomal formulation of the present invention would provide a significant advantage in the treatment of microbial antibiotic resistance due increased circulation time, lower toxicity, and increased penetration of the agent through the outer membrane and mucoid exopolysaccharides such as those secreted by mucoid variants of bacteria like *Pseudomonas aeruginosa*.

EXAMPLE 11

Use of Liposomes Against *Pneumoeystis carinii* Infection

*Pneumocystis carinii* pneumonia (PCP) is a severe problem for immunocompromised patients, particularly those with AIDS. PCP affects the lungs, as well as other parts of the body, including the skin and internal organs. The antiparasitic drug, pentamidine, has been used for the treatment and prophylaxis of PCP. However, pentamidine has severe side effects which could be obviated by proper targeting to the affected organs. This would also remove the need for high dosages that exacerbate the side effects. Use of pentamidine in aerosol form in an animal model has shown no harmful effects (Wei, C. C. et al., 1998, Chest 114:742–747). Pentamidine may be used in the liposomal formulation of the present invention and used in the prophylaxis and treatment of PCP.

The results presented herein showing a significant microbicidal efficacy of the liposomal formulation comparative to free agents compared to the different bacteria and fungi used, show that the antimicrobial property of this formulation cannot be restricted to a particular type of cell and indicate that the liposomal formulations of the present invention could be effectively used for killing microbes in general. Furthermore, the formulations of the invention may be used to deliver an agent to virtually any cell type.

In summary the present liposomal formulations provide a very significant improvement in the delivery of agents as compared to those of the prior art. These formulations could be used in numerous animal and cell systems.

Other Embodiments

All publications and patent applications mentioned in this specification, including Lagacé et al., 1996, WO 96/19972 and Lagacé et al., 1997, U.S. Pat. No. 5,662,929, are herein incorporated by reference to the same extent as if each independent publication or patent application was specifically and individually indicated to be incorporated by reference.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

We claim:

1. A method for killing a fungus, said method comprising administering a pharmaceutically effective amount of a low-rigidity liposomal formulation, wherein said formulation (i) is free of cholesterol;

(ii) comprises neutral and anionic phospholipids at a molar ratio of greater than 10:1, said molar ratio not greater than 20:1;

(iii) has a phase transition temperature (Tc) below 42° C. as measured by DSC; and (iv) comprises at least one antifungal agent, wherein said formulation has enhanced antifungal activity relative to the same amount of the free antifungal agent.

2. The method of claim 1, wherein said method includes treating, preventing or diagnosing a fungal infection in a mammal.

3. The method of claim 1, wherein said fungus is a drug-resistant fungus.

4. The method of claim 2, wherein said mammal is a human.

5. The method of claim 2, wherein said infection is caused by at least one yeast.

6. The method of claim 5, wherein said yeast is selected from the group consisting of Candida, Histoplasma, Blastomyces, Coccidioides, Aspergillus, Mucomycosis, Microsporum, Epidermophyton, Trichophyton, and Cryptococcus.

7. The method of claim 5, wherein said infection is a respiratory infection in an immunocompromised patient and said yeast is Candida or *Aspergillus fumigatus*.

8. A method of killing a fungus a viva, said method comprising administering a pharmaceutically effective amount of a low-rigidity liposomal formulation, wherein said formulation
   (i) is free of cholesterol;
   (ii) comprises neutral and anionic phospholipids at a molar ratio of greater than 10:1, said molar ratio not greater than 20:1;
   (iii) has a phase transition temperature (Tc) below 42° C. as measured by DSC; and
   (iv) comprises at least one antifungal agent, wherein said formulation has enhanced antifungal activity relative to the sonic amount of the free antifungal agent.

9. The method of claim 8, wherein said fungus is in a cell culture medium.

10. A method of introducing an antimicrobial agent into a fungal or bacterial cell, said method comprising administering a pharmaceutically effective amount of a low-rigidity liposomal formulation, wherein said formulation
    (i) is free of cholesterol;
    (ii) comprises neutral and anionic phospholipids at a molar ratio of greater than 20:1, said molar ratio not greater than 20:1;
    (iii) has a phase transition temperature (Tc) below 42° C. as measured by DSC; and
    (iv) comprises at least one antimicrobial agent, wherein said formulation has enhanced antimicrobial activity relative to the same amount of the free antimicrobial agent.

11. A method of making a low-rigidity liposomal formulation, said formulation being free of cholesterol, comprising neutral and anionic phospholipids at a molar ratio of greater than 10:1, said molar ratio not greater than 20:1, having a phase transition temperature (Tc) below 42° C. as measured by DSC, and comprising at least one antimicrobial agent, wherein said formulation has enhanced antimicrobial activity relative to the same amount of the free antimicrobial agent, said method comprising the steps:
    a) mixing said neutral and anionic phospholipids in a solution;
    b) evaporating said solution to form a lipid film;
    c) hydrating said lipid film with an aqueous solution comprising an antimicrobial agent;
    d) extruding the hydrated lipid film of (c) through a suitable porous material, said method lacking a lyophilization step.

12. A low-rigidity liposomal formulation, said formulation being free of cholesterol, comprising neutral and anionic phospholipids at a molar ratio of greater than 10:1, said molar ratio not greater than 20:1, having a phase transition temperature (Tc) below 42° C. as measured by DSC, further comprising an antimicrobial agent, and wherein said formulation enhances the antimicrobial activity of an antimicrobial agent relative to the same amount of the free antimicrobial agent.

13. The liposomal formulation of claim 12, wherein said formulation further comprises an antimicrobial agent.

14. The liposomal formulation of claim 12, wherein said neutral and anionic phospholipids are present at a molar ratio of greater than 10:1, said molar ratio not greater than 15:1.

15. The liposomal formulation of claim 12, wherein said neutral phospholipid is selected from the group consisting of dipalmitoylphosphatidylcholine (DPPC) and 1,2-di-o-hexadecyl-sn-glycero-3-phosphocholine (DHPC).

16. The liposomal formulation of claim 12, wherein said anionic phospholipid is selected from the group consisting of dimirystoyl-phosphatidylglycerol (DMPG) and soybean 1-α-phosphatidylinositol (PI).

17. The liposomal formulation of claim 13, wherein said antimicrobial agent is a fungicide.

18. The liposomal formulation of claim 17, wherein said fungicide is amphotericin B at a concentration from 0.1 µg/ml to 500 mg/ml.

19. The liposomal formulation of claim 13, wherein said antimicrobial agent is a nucleic acid or nucleotide analog.

20. The method of claims 1, 8, 10, or 11, wherein said neutral and anionic phospholipids are present at a molar ratio of greater than 10:1, said molar ratio not greater than 15:1.

* * * * *

UNITED STATES PATENT AND TRADEMARK OFFICE
CERTIFICATE OF CORRECTION

PATENT NO. : 6,613,352 B2
DATED : September 2, 2003
INVENTOR(S) : Lagace et al.

It is certified that error appears in the above-identified patent and that said Letters Patent is hereby corrected as shown below:

Column 3,
Lines 33 and 34, "ug" should be -- µg --.
Line 51, "comprising comprising" should be -- comprising --.

Column 7,
Line 29, "inflamammary" should be -- inframammary --.

Column 11,
Lines 15 and 20, "diluant" should be -- diluent --.
Line 16, "Diluant" should be -- Diluent --.

Column 12,
Lines 29-30, "Disteroylphosphatidylcholine" should be
-- Distearoylphosphatidylcholine --.
Line 56, Table 2, "Destablization" should be -- Destabilization --.

Column 13,
Line 27, "intracheally" should be -- intratracheally --.
Table 3, "(ug/pair of lungs)" should be -- (µg/pair of lungs) --; "(ug/pair of kidneys)" should be -- (µg/pair of kidneys) --; and "(ug/ml)" should be -- (µg/ml) --.

Column 14,
Line 24, "homogeneized" should be -- homogenized --.

Column 15,
Line 59, "*aerguinosa*" should be -- *aeruginosa* --.
Line 65, "aminolycosides" should be -- aminoglycosides --.

Column 16,
Line 63, "lipoplysaccaride" should be -- lipopolysaccharide --.

Column 17,
Line 2, "polysaccarides" should be -- polysaccharides --.
Line 20, "lipopolysaccarides" should be -- lipopolysaccharides --.

UNITED STATES PATENT AND TRADEMARK OFFICE
CERTIFICATE OF CORRECTION

PATENT NO. : 6,613,352 B2
DATED : September 2, 2003
INVENTOR(S) : Lagace et al.

It is certified that error appears in the above-identified patent and that said Letters Patent is hereby corrected as shown below:

<u>Column 18,</u>
Line 5, "liposonal" should be -- liposomal --.
Line 67, "ar" should be -- at --.

<u>Column 19,</u>
Line 10, "withing" should be -- within --.
Line 63, "*Pneumoeystis*" should be -- *Pneumocystis* --.

Signed and Sealed this

Sixth Day of June, 2006

JON W. DUDAS
*Director of the United States Patent and Trademark Office*